(12) United States Patent
Ishida et al.

(10) Patent No.: US 7,045,651 B2
(45) Date of Patent: May 16, 2006

(54) PRODUCTION PROCESS FOR HYDROXYALKYL (METH) ACRYLATE

(75) Inventors: Tokumasa Ishida, Himeji (JP); Masahiro Uemura, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/435,992

(22) Filed: May 12, 2003

(65) Prior Publication Data

US 2003/0229243 A1    Dec. 11, 2003

(30) Foreign Application Priority Data

Jun. 11, 2002 (JP) .............................. 2002-170515

(51) Int. Cl.
*C07C 67/26* (2006.01)
(52) U.S. Cl. ...................................... 560/200; 560/209
(58) Field of Classification Search ................ 560/209, 560/240, 218, 4, 129, 205, 200, 224
See application file for complete search history.

(56) References Cited

U.S. PATENT DOCUMENTS

| | | | | |
|---|---|---|---|---|
| 3,399,229 A | * | 8/1968 | Wilhelm et al. | 560/200 |
| 3,632,854 A | * | 1/1972 | Randall | 560/200 |
| 4,017,429 A | * | 4/1977 | Steele et al. | 560/200 |
| 4,365,081 A | * | 12/1982 | Shimizu et al. | 560/209 |
| 4,404,395 A | * | 9/1983 | Markiewitz | 560/209 |
| 4,910,329 A | * | 3/1990 | McDade | 560/209 |
| 6,414,182 B1 | | 7/2002 | Shingai et al. | |
| 6,465,681 B1 | | 10/2002 | Uemura et al. | |
| 2002/0198403 A1 | | 12/2002 | Kubo | |

FOREIGN PATENT DOCUMENTS

| | | |
|---|---|---|
| DE | 1 147 938 | 5/1963 |
| JP | 10-237022 A | 9/1998 |
| JP | 2001-348362 A | 12/2001 |
| JP | 2003-55304 A | 2/2003 |
| WO | WO 02/076919 A1 | 10/2002 |

\* cited by examiner

*Primary Examiner*—Cecilia J. Tsang
*Assistant Examiner*—Taylor Victor Oh

(57) ABSTRACT

The present invention provides a novel production process for a hydroxyalkyl (meth)acrylate, in which it is possible that: in a batch reaction system, the amount of the hydroxyalkyl (meth)acrylate (which is the objective product) as produced is kept nearly on the same level as conventional and further, at the same time, there is suppressed the side production of the alkylene oxide's diaddition product (dialkylene glycol mono(meth)acrylate) that lowers the purity of the product to thus give a bad influence upon its quality. The present invention production process comprises the step of carrying out a batch reaction between (meth)acrylic acid and an alkylene oxide in the presence of a catalyst in order to produce the hydroxyalkyl (meth)acrylate; with the production process being characterized by arranging that the reaction should be initiated in a state of a catalyst concentration of more than 1, wherein the catalyst concentration is defined as the amount of the catalyst as used relative to the integrated amount of the (meth)acrylic acid as supplied and is assumed to be 1 in terms of the amount of the entire catalyst to be used relative to the amount of the entire (meth)acrylic acid to be supplied.

7 Claims, No Drawings

PRODUCTION PROCESS FOR HYDROXYALKYL (METH) ACRYLATE

BACKGROUND OF THE INVENTION

A. Technical Field

The present invention relates to a production process for a hydroxyalkyl (meth)acrylate, which comprises the step of carrying out a reaction between (meth)acrylic acid and an alkylene oxide in the presence of a catalyst.

B. Background Art

What have hitherto been common as production processes for a hydroxyalkyl (meth)acrylate involving a batch reaction between (meth)acrylic acid and an alkylene oxide are: a process that involves the step of charging a reaction vessel with (meth)acrylic acid and an alkylene oxide (which are raw materials) along with a catalyst in a lump to thus carry out their reaction; and a process that involves the steps of charging a reaction vessel with (meth)acrylic acid (which is a raw material) and a catalyst both in their entirety and thereafter adding an alkylene oxide thereto gradually (continuously or intermittently) at a constant or variable supplying rate to thus carry out their reaction. The reasons therefor are such that: the (meth)acrylic acid has higher catalyst-dissolving ability than the alkylene oxide; and, if the alkylene oxide is initially charged alone into the reaction vessel and then heated, there is involved a danger of explosion, and therefore special facilities for coping with this danger are needed. Even in the former process that involves the step of charging the reaction vessel with the (meth)acrylic acid and the alkylene oxide along with the catalyst in a lump to thus carry out their reaction, it is actually a conventional procedure to charge the (meth)acrylic acid earlier than the alkylene oxide.

However, both in the above processes, there is a problem such that: a dialkylene glycol mono(meth)acrylate (which is an alkylene oxide's diaddition product and may hereinafter be referred to simply as "alkylene oxide's diaddition product") tends to be by-produced as an impurity, therefore the resultant product is so low in purity as to be bad in quality. In addition, as a matter of fact, the alkylene oxide's diaddition product as by-produced can be removed in the distillation step after the reaction step. However, it is inevitable that, as the alkylene oxide's diaddition product is more and more by-produced in the reaction step, the yield of the hydroxyalkyl (meth)acrylate (which is the objective product) becomes lower. Therefore, as to the reaction stage, it is strongly desired to suppress the side production of the above alkylene oxide's diaddition product as much as possible, with the amount of the produced objective product kept as large as conventional, or larger.

SUMMARY OF THE INVENTION

A. Object of the Invention

Thus, an object of the present invention is to provide a novel production process for a hydroxyalkyl (meth)acrylate, in which it is possible that: in a batch reaction system, the amount of the hydroxyalkyl (meth)acrylate (which is the objective product) as produced is kept nearly on the same level as conventional and further, at the same time, there is suppressed the side production of the alkylene oxide's diaddition product that lowers the purity of the product to thus give a bad influence upon its quality.

B. Disclosure of the Invention

The present inventors diligently studied to solve the above-mentioned problems. As a result, they have found out that: if, when the batch reaction between the (meth)acrylic acid and the alkylene oxide (which are raw materials) is carried out, it is arranged that the reaction should be initiated in such a manner that the concentration of the catalyst relative to the (meth)acrylic acid is more than a specific value, then the side production of the alkylene oxide's diaddition product (which is an impurity) can be suppressed much more than conventional. In addition, they have further confirmed that the amount of the objective product as produced by such a production process is on the same level as of conventional batch reaction systems.

The present inventors have completed the present invention by confirming that the production process as mentioned above could solve the aforementioned problems at a stroke.

That is to say, a production process for a hydroxyalkyl (meth)acrylate, according to the present invention, comprises the step of carrying out a batch reaction between (meth)acrylic acid and an alkylene oxide in the presence of a catalyst in order to produce the hydroxyalkyl (meth)acrylate; with the production process being characterized by arranging that the reaction should be initiated in a state of a catalyst concentration of more than 1, wherein the catalyst concentration is defined as the amount of the catalyst as used relative to the integrated amount of the (meth)acrylic acid as supplied and is assumed to be 1 in terms of the amount of the entire catalyst to be used relative to the amount of the entire (meth)acrylic acid to be supplied.

These and other objects and the advantages of the present invention will be more fully apparent from the following detailed disclosure.

DETAILED DESCRIPTION OF THE INVENTION

Hereinafter, detailed descriptions are given about the production process for a hydroxyalkyl (meth)acrylate according to the present invention (which may hereinafter be referred to as present invention production process). However, the scope of the present invention is not bound to these descriptions. And other than the following illustrations can also be carried out in the form of appropriate modifications of the following illustrations within the scope not departing from the spirit of the present invention.

First of all explained are outlines of conventional production processes for the hydroxyalkyl (meth)acrylate to which the present invention production process is favorably applicable. Specifically, the (meth)acrylic acid and the alkylene oxide (which are raw reaction materials) are first caused to react with each other in the presence of the catalyst. The conversion of this reaction is frequently less than 100%, and therefore it is common that such as unreacted (meth)acrylic acid and unreacted alkylene oxide remain in the resultant reaction liquid at the end of the reaction. Thus, the above reaction liquid is led to the step for removing such as these unreacted raw materials from the reaction liquid. Then, as the subsequent final stage, the purification is carried out by such as distillation, thus obtaining the objective hydroxyalkyl (meth)acrylate.

The present invention production process is a production process comprising the step of carrying out batchwise a reaction (carrying out a batch reaction) between the (meth)acrylic acid and the alkylene oxide (which are raw reaction materials) in the presence of the catalyst in order to obtain the hydroxyalkyl (meth)acrylate. Then, this production process is characterized by arranging that the reaction between the (meth)acrylic acid and the alkylene oxide should be initiated in a state of a catalyst concentration of more than 1 (in other words, the reaction system should be in a state where the catalyst concentration is more than 1 at the beginning of the reaction), wherein the "catalyst concentration" is defined as the ratio of the integrated amount of the catalyst as used and added relative to the integrated amount of the (meth)acrylic acid as supplied and further is assumed to be 1 in terms of a value determined as the ratio of the amount of the entire catalyst to be used to the amount of the entire (meth)acrylic acid to be supplied.

In the present invention, when there have been satisfied the following requirements that: ① the catalyst should be present; ② the temperature should not be lower than a predetermined temperature (specifically, 40° C.); and ③ there should coexist both raw reaction materials above; the reaction begins and, if at least one of ① to ③ above is lacked, then the reaction does not occur. Therefore, the beginning of the reaction in the present invention means a point of time when the above-mentioned lacked requirement becomes satisfied, and it is important in the present invention to arrange that the catalyst concentration, as determined from the integrated amount of the (meth)acrylic acid and the integrated amount of the catalyst as used which have been added (charged) by this point of time of the beginning of the reaction, should be more than 1. The above beginning of the reaction is, for specific example, as follows: if the reaction system temperature is not lower than 40° C. at a point of time when both raw reaction materials above have been added (supplied), then the above beginning of the reaction means this point of time; and, if the reaction system temperature is lower than 40° C. at the point of time when both raw reaction materials above have been added (supplied), then the above beginning of the reaction means a point of time when the reaction system temperature has reached not lower than 40° C. due to such as the subsequent rise of the temperature; and, if at least a portion of each of both raw reaction materials above is initially charged, then the above beginning of the reaction means a point of time when the reaction system temperature has reached not lower than 40° C. due to such as the subsequent rise of the temperature.

On the other hand, the end of the reaction in the present invention means a point of time when the acid content of the reaction liquid has decreased to not more than 0.5 weight % after the above beginning of the reaction.

Incidentally, the catalyst concentration after the beginning of the reaction (e.g. catalyst concentration while the reaction is going on) is defined as the ratio of the integrated amount of the catalyst as used and added by any point of time of from the above beginning of the reaction to the above end of the reaction to the integrated amount of the (meth)acrylic acid as, for example, supplied to the reaction system by this point of time.

As is described above, in the present invention production process, it is arranged that the reaction should be initiated with the reaction system being put in a state where the catalyst concentration is more than 1, favorably in the range of 1.1 to 20, more favorably 1.2 to 10. In the case where the catalyst concentration is not more than 1 at the beginning of the reaction, there is a possibility that the aforementioned problems cannot be solved. In addition, in the present invention, it is favorable that the reaction system is put in a state where the catalyst concentration is more than 1 for as much time as possible of from the beginning of the reaction to the end of the reaction. Specifically, it is particularly favorable that the conditions of supplying the raw materials are set so that the supply of the amount of the entire (meth)acrylic acid to be supplied will be completed at the same time as or after the completion of the supply of the amount of the entire alkylene oxide to be supplied.

As to quantitative relations between the amount of the entire (meth)acrylic acid to be supplied and the amount of the entire alkylene oxide to be supplied in the present invention production process, the amount of the alkylene oxide is favorably in the range of 1.0 to 10 mols, more favorably 1.0 to 5.0 mols, still more favorably 1.0 to 3.0 mols, particularly favorably 1.0 to 2.0 mols, per 1 mol of the (meth)acrylic acid. In the case where the amount of the alkylene oxide is smaller than 1.0 mol per 1 mol of the (meth)acrylic acid, there is a possibility that: the reaction may not run, therefore the present invention characteristic production process cannot be carried out. In addition, in the case where the amount of the alkylene oxide is larger than 10 mols per 1 mol of the (meth)acrylic acid, there is a possibility that: such as the step of recovering the alkylene oxide may be needed and therefore inflict an economical loss.

Though not especially limited, the alkylene oxide usable in the present invention production process is favorably an alkylene oxide having 2 to 6 carbon atoms, more favorably 2 to 4 carbon atoms. Examples thereof include ethylene oxide, propylene oxide, and butylene oxide. The ethylene oxide and the propylene oxide are favorable. In addition, the (meth)acrylic acid usable in the present invention means acrylic acid and/or methacrylic acid. Incidentally, in the present invention and the present specification, as to the hydroxyalkyl (meth)acrylate (which is the objective product) and as to the alkylene glycol di(meth)acrylate and the dialkylene glycol mono(meth)acrylate as by-products and impurities, the "(meth)acrylate" portion of these compounds' names is defined as having two meanings of "acrylate" and "methacrylate", in detail, as follows: when the above (meth)acrylic acid (which is a raw material) is acrylic acid, the "(meth)acrylate" is defined as meaning "acrylate" in derivation from the acrylic acid; and, when the above (meth)acrylic acid (which is a raw material) is methacrylic acid, the "(meth)acrylate" is defined as meaning "methacrylate" in derivation from the methacrylic acid.

The batch reaction between the (meth)acrylic acid and the alkylene oxide in the presence of the catalyst in the present invention production process can be carried out in such a manner that the conditions and procedures other than the above characteristics of the present invention are based on processes as commonly used for this kind of reaction or on processes similar thereto. Specifically, the reaction is usually initiated by adding the raw alkylene oxide into where the raw (meth)acrylic acid has been charged. However, in a stage when a portion of the amount of the entire raw (meth)acrylic acid to be supplied is initially charged in the present invention, it is permitted that: a portion of the amount of the entire raw alkylene oxide to be supplied is also charged together, and then the reaction is initiated. The above addition of the alkylene oxide may be either lump-sum addition or gradual addition, but is favorably the gradual addition, namely, continuous and/or intermittent addition (which may hereinafter be referred to as "continuous addition" and "intermittent addition" respectively). Then, as is often carried out in this kind of reaction, it is also possible that: the reaction is continued still after the addition of the amount of the entire raw alkylene oxide to be supplied has been completed, thus carrying out what is called aging to complete the reaction.

The above gradual addition means a mode which is not what is called lump-sum addition such that the amount of the entire alkylene oxide to be supplied is all at once added to a reaction vessel. The continuous addition means gradual addition such that the material is continuously added little by little, and the intermittent addition means gradual addition such that the material is pulsewise or intermittently added divisionally into any number of times, for example, the material is intermittently added divisionally into two or three times.

In the case where the above continuous addition is carried out, the continuous addition may be run with the addition rate kept constant until the end of the addition, or may be run with the addition rate changed at least once on the way, or may be run while the rate itself is varied continuously and arbitrarily. Thus, the mode for the continuous addition is not especially limited. In the case of changing the rate at least once on the way, it is favorable to reduce the rate from that before the change to that after the change.

As mentioned below, in the present invention production process, it is permitted as to the catalyst as used either that its entirety to be used is charged at the beginning of the reaction, or that: only a portion of it is charged at the beginning of the reaction and then the rest is appropriately additionally used.

In the present invention production process, it is arranged that a portion of the entire raw (meth)acrylic acid to be supplied should initially be charged before the beginning of the reaction and/or supplied at the beginning of the reaction. There is no especial limitation on the total amount of these portions, as initially charged before the beginning of the reaction and/or supplied at the beginning of the reaction, of the (meth)acrylic acid if this total amount is such that the catalyst concentration at the beginning of the reaction can satisfy the aforementioned range. Specifically, the aforementioned total amount is favorably not larger than 90 weight %, more favorably in the range of 5 to 90 weight %, still more favorably 10 to 75 weight %, particularly favorably 20 to 50 weight %, relative to the amount of the entire (meth)acrylic acid to be supplied (in the case where the entire catalyst to be used is charged not later than the beginning of the reaction) or relative to a predetermined amount of (meth)acrylic acid (i.e. "amount of entire (meth) acrylic acid to be supplied×(amount of a portion of entire catalyst to be used)/(amount of entire catalyst to be used)") (in the case where only a portion of the entire catalyst to be used is charged not later than the beginning of the reaction). If the total amount of such as the initially charged portion of the (meth)acrylic acid is set in the above range, the catalyst concentration relative to the above total amount can be set to be relatively high, and there are satisfied the conditions of the catalyst concentration (the state where the catalyst concentration is more than 1) at the beginning of the reaction, which conditions are characteristics of the present invention production process. Therefore, the aforementioned object can easily be achieved. In addition, there can further be obtained effects such as the increase of the reaction rate and the enhancement of the productivity.

In the present invention production process, the reaction is, as aforementioned, initiated in a manner such that a portion of the amount of the entire raw (meth)acrylic acid to be supplied is initially charged. Above all, it is favorable that: only a portion of the amount of the entire raw alkylene oxide to be supplied is first charged together with the above initially charged portion of the (meth)acrylic acid to thereby initiate the reaction, or is added (supplied) to the above initially charged portion of the (meth)acrylic acid by the lump-sum addition or gradual addition to thereby initiate the reaction. That is to say, in the initial stage of the reaction, it is favorable to arrange that only a portion of the amount of the entire raw alkylene oxide to be supplied should be added without adding the residual (meth)acrylic acid other than the initially charged portion, and it is favorable that this mode of adding only the alkylene oxide is continued, for example, until the amount of the alkylene oxide as added reaches such an amount as satisfies the below-mentioned conditions. Incidentally, the explanation about the gradual addition is the same as aforementioned.

As to the above addition (supply) of only the alkylene oxide from the beginning of the reaction, the amount of the alkylene oxide as added is favorably in the range of 0.8 to 2.0, more favorably 0.8 to 1.5, still more favorably 0.9 to 1.5, particularly favorably 1.0 to 1.3, in terms of molar ratio to the amount of the (meth)acrylic acid as initially charged. In the case where the above molar ratio is less than 0.8, there is a possibility that an alkylene glycol di(meth)acrylate (which is a diester) may be by-produced. In the case where the above molar ratio is more than 2.0, there is a possibility that the dialkylene glycol mono(meth)acrylate (which is the alkylene oxide's diaddition product) may tend to be by-produced to lower the distillate yield or the purity. Incidentally, the amount of the alkylene oxide as added (supplied) so as to be in the above molar ratio range is favorably set appropriately by beforehand reckoning it from the amount of the (meth)acrylic acid as initially charged, and may be regarded as reaching the above molar ratio range at a stage when the addition of the above set amount as added has been completed.

As to the above addition of only the alkylene oxide, the alkylene oxide as added may have ordinary temperature or may beforehand be heated to the below-mentioned desirable reaction temperature.

As to the above addition of only the alkylene oxide, the time to complete the addition is favorably within 5 hours, more favorably in the range of 0.01 to 5 hours, still more favorably 0.1 to 5 hours, from the beginning of the reaction. In the case where the above supplying time is longer than 5 hours, there is a possibility that the alkylene glycol di(meth) acrylate (which is a diester) may be by-produced.

In the present invention production process, after the end of the above addition of only the alkylene oxide, for example, it is favorable to arrange that the residual raw (meth)acrylic acid and the residual raw alkylene oxide should be added and supplied together by the lump-sum addition or gradual addition. Incidentally, the explanation about the gradual addition is the same as aforementioned. Incidentally, in the case where, as is aforementioned, the initially added portion of the amount of the entire alkylene oxide to be supplied is charged together with the initially charged portion of the (meth)acrylic acid to thus carry out the reaction, it is favorable that the residual raw (meth) acrylic acid and the residual raw alkylene oxide are added thereto at a point of time when 0.01 to 5 hours (more favorably 0.1 to 5 hours) have passed since the beginning of the reaction. In the case of outside the above range, there is a possibility that the dialkylene glycol mono(meth)acrylate (which is the alkylene oxide's diaddition product) may tend to be by-produced to lower the distillate yield or the purity.

As to the addition (supply) of the residual raw (meth) acrylic acid and the residual raw alkylene oxide, the amount of the alkylene oxide as added is favorably set to be in the range of 0.8 to 2.0, more favorably 0.8 to 1.5, still more favorably 0.9 to 1.5, in terms of molar ratio to the amount of the (meth)acrylic acid as added. In the case where the above molar ratio is less than 0.8, there is a possibility that the alkylene glycol di(meth)acrylate (which is a diester) may be by-produced. In the case where the above molar ratio is more than 2.0, there is a possibility that the dialkylene glycol mono(meth)acrylate (which is the alkylene oxide's diaddition product) may tend to be by-produced to lower the distillate yield or the purity.

As to the addition (addition to the reactor) of the residual raw (meth)acrylic acid and the residual raw alkylene oxide, they may be added from their respective different addition lines, or they may be added after having beforehand been mixed together by using such as piping, a line mixer, or a mixing tank before being added to the reactor, therefore there is no especial limitation. However, in the case of the addition from their respective different addition lines, for example, the molar ratio of the (meth)acrylic acid in the reaction liquid is excessive in the neighborhood of a place to which the (meth)acrylic acid is added, therefore it is favorable that the above raw materials are added after having beforehand been mixed together by using such as piping before being added (to the reactor). In addition, the residual raw (meth)acrylic acid and the residual raw alkylene oxide may be added under ordinary temperature or after having beforehand been heated to the below-mentioned desirable reaction temperature.

As to the addition of the residual raw (meth)acrylic acid and the residual raw alkylene oxide, the addition (supplying) time is favorably in the range of 0.1 to 5 hours, more favorably 0.1 to 4 hours, still more favorably 0.1 to 3 hours. In the case where the above addition (supplying) time is shorter than 0.1 hour, there is a possibility that there may be economical disadvantages such that the quantity of the reaction heat as generated per hour is so large that the heat exchanger for cooling must be enlarged. In the case where the addition (supplying) time is longer than 5 hours, there is a possibility that the productivity may be low.

As to such as the modes of the addition (lump-sum addition, gradual addition), the temperatures of the raw materials, and the addition (supplying) time in the case where the residual raw (meth)acrylic acid and the residual raw alkylene oxide are added from their respective different addition lines, it is enough that each raw material individually satisfies the above subject-matter or ranges, and thus they do not necessarily need to be made the same.

There is no especial limitation on the catalyst usable for reaction in the present invention production process. However, specific favorable examples thereof include catalysts including at least one member selected from the group consisting of: chromium (Cr) compounds, iron (Fe) compounds, yttrium (Y) compounds, lanthanum (La) compounds, cerium (Ce) compounds, tungsten (W) compounds, zirconium (Zr) compounds, titanium (Ti) compounds, vanadium (V) compounds, phosphorus (P) compounds, aluminum (Al) compounds, molybdenum (Mo) compounds, and amine compounds; and homogeneous catalysts are more favorable.

There is no especial limitation on the chromium (Cr) compound if it is a compound containing a chromium (Cr) atom in its molecule and is soluble in the aforementioned reaction liquid. Specific examples thereof include chromium chloride, chromium acetylacetonate, chromium formate, chromium acetate, chromium acrylate, chromium methacrylate, sodium bichromate, and chromium dibutyldithiocarbamate.

There is no especial limitation on the iron (Fe) compound if it is a compound containing an iron (Fe) atom in its molecule and is soluble in the aforementioned reaction liquid. Specific examples thereof include iron powders, iron chloride, iron formate, iron acetate, iron acrylate, and iron methacrylate.

There is no especial limitation on the yttrium (Y) compound if it is a compound containing an yttrium (Y) atom in its molecule and is soluble in the aforementioned reaction liquid. Specific examples thereof include yttrium acetylacetonate, yttrium chloride, yttrium acetate, yttrium nitrate, yttrium sulfate, yttrium acrylate, and yttrium methacrylate.

There is no especial limitation on the lanthanum (La) compound if it is a compound containing a lanthanum (La) atom in its molecule and is soluble in the aforementioned reaction liquid. Specific examples thereof include lanthanum acetylacetonate, lanthanum chloride, lanthanum acetate, lanthanum nitrate, lanthanum sulfate, lanthanum acrylate, and lanthanum methacrylate.

There is no especial limitation on the cerium (Ce) compound if it is a compound containing a cerium (Ce) atom in its molecule and is soluble in the aforementioned reaction liquid. Specific examples thereof include cerium acetylacetonate, cerium chloride, cerium acetate, cerium nitrate, cerium sulfate, cerium acrylate, and cerium methacrylate.

There is no especial limitation on the tungsten (W) compound if it is a compound containing a tungsten (W) atom in its molecule and is soluble in the aforementioned reaction liquid. Specific examples thereof include tungsten chloride, tungsten acrylate, and tungsten methacrylate.

There is no especial limitation on the zirconium (Zr) compound if it is a compound containing a zirconium (Zr) atom in its molecule and is soluble in the aforementioned reaction liquid. Specific examples thereof include zirconium acetylacetonate, zirconium chloride, zirconium acetate, zirconium nitrate, zirconium sulfate, zirconium acrylate, zirconium methacrylate, zirconium butoxide, zirconium propoxide, zirconyl chloride, zirconyl acetate, zirconyl nitrate, zirconyl acrylate, and zirconyl methacrylate.

There is no especial limitation on the titanium (Ti) compound if it is a compound containing a titanium (Ti) atom in its molecule and is soluble in the aforementioned reaction liquid. Specific examples thereof include titanium chloride, titanium nitrate, titanium sulfate, titanium methoxide, titanium ethoxide, titanium propoxide, titanium isopropoxide, titanium acrylate, and titanium methacrylate.

There is no especial limitation on the vanadium (V) compound if it is a compound containing a vanadium (V) atom in its molecule and is soluble in the aforementioned reaction liquid. Specific examples thereof include vanadium acetylacetonate, vanadium chloride, vanadium naphthenate, vanadium acrylate, and vanadium methacrylate.

There is no especial limitation on the phosphorus (P) compound if it is a compound containing a phosphorus (P) atom in its molecule and is soluble in the aforementioned reaction liquid. Specific examples thereof include: alkylphosphines, such as trimethylphosphine, tributylphosphine, trioctylphosphine, triphenylphosphine, tritolylphosphine, and 1,2-bis(diphenylphosphine)ethane; and their quaternary phosphonium salts such as (meth)acrylate salts.

There is no especial limitation on the aluminum (Al) compound if it is a compound containing an aluminum (Al) atom in its molecule and is soluble in the aforementioned reaction liquid. Specific examples thereof include aluminum acetylacetonate, aluminum chloride, aluminum acetate, aluminum nitrate, aluminum sulfate, aluminum ethoxide, aluminum isopropoxide, aluminum acrylate, and aluminum methacrylate.

There is no especial limitation on the molybdenum (Mo) compound if it is a compound containing a molybdenum (Mo) atom in its molecule and is soluble in the aforementioned reaction liquid. Specific examples thereof include molybdenum chloride, molybdenum acetate, molybdenum acrylate, and molybdenum methacrylate.

There is no especial limitation on the amine compound if it is a compound containing an amine functional group in its molecule. Specific examples thereof include: homogeneous amine compounds, such as trialkylamines, cyclic amines (e.g. pyridine), and their quaternary salts; and heterogeneous amine compounds, such as basic anion-exchange resins containing at least one kind of basic functional group (e.g. a tertiary amino group, a quaternary ammonium group, and a pyridinium group). The amine compound is favorably the basic anion-exchange resin containing at least one kind of basic functional group (e.g. a tertiary amino group, a quaternary ammonium group, and a pyridinium group), and is more favorably a basic anion-exchange resin containing at least one kind of functional group selected from the group consisting of tertiary amino groups, quaternary ammonium groups, and pyridinium groups.

If the above amine compound is used as a portion of the catalyst, there are obtained effects such that: the synergistic effect is seen as to the catalytic activity, and the reaction conversion is enhanced, and further the reaction selectivity is also enhanced.

There is no especial limitation on the amount of the entire above catalyst to be used in the present invention production process. However, in the case of the homogeneous catalyst, this amount is favorably in the range of 0.001 to 10 mol %, more favorably 0.005 to 5 mol %, still more favorably 0.01 to 3 mol %, relative to the amount of the entire raw (meth)acrylic acid to be supplied. In the case where the amount is smaller than 0.001 mol %, there is a possibility that: the reaction rate may be too slow, therefore the reaction time may be so long as to result in low productivity. In the case where the amount is larger than 10 mol %, there is a possibility that the reaction selectivity of the by-product may be high. Furthermore, as to the homogeneous catalyst, it is usually common that the amount of the entire catalyst to be used is beforehand added (charged) to the reaction vessel before the beginning of the reaction. However, if the catalyst concentration as referred to in the present invention can be set to be in the aforementioned range at the beginning of the reaction, then the amount of the catalyst as initially added (i.e. the amount of the charged catalyst at the beginning of the reaction) is not limited to the amount of the entire catalyst to be used, but may be a portion thereof. In this case, the residual portion may be supplied on the way of the progress of the reaction. In addition, in the case of the homogeneous catalyst, it may be charged or supplied into the reaction vessel after having beforehand been dissolved into either of both raw materials and, for example, it may be charged or added and supplied into the reaction vessel together with the raw (meth)acrylic acid after having been dissolved into the raw (meth)acrylic acid in a dissolution tank different from the reaction vessel.

On the other hand, in the case of the heterogeneous catalyst, there is no especial limitation on the amount of the entire catalyst to be used. However, in the batch reaction, this amount is favorably in the range of 5 to 80 weight %, more favorably 10 to 70 weight %, relative to the amount of the entire raw (meth)acrylic acid to be supplied.

In the present invention production process, a polymerization inhibitor can be added to the reaction liquid, if necessary. There is no especial limitation on the polymerization inhibitor, and any one is usable if it is a polymerization inhibitor as commonly industrially used. Specific examples thereof include: phenol compounds, such as hydroquinone, methylhydroquinone, tert-butylhydroquinone, 2,6-di-tert-butylhydroquinone, 2,5-di-tert-butylhydroquinone, 2,4-dimethyl-6-tert-butylphenol, and hydroquinone monomethyl ether; p-phenylenediamines, such as N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N,N'-diphenyl-p-phenylenedianine, and N,N'-di-2-naphthyl-p-phenylenediamine; amine compounds, such as thiodiphenylamine and phenothiazine; copper dialkyldithiocarbamates, such as copper dibutyldithiocarbamate, copper diethyldithiocarbamate, and copper dimethyldithiocarbamate; and N-oxyl compounds, such as 2,2,4,4-tetramethylazetidine-1-oxyl, 2,2-dimethyl-4,4-dipropylazetidine-1-oxyl, 2,2,5,5-tetramethylpyrrolidine-1-oxyl, 2,2,5,5-tetramethyl-3-oxopyrrolidine-1-oxyl, 2,2,6,6-tetramethylpiperidine-1-oxyl, 4-hydroxy-2,2,6,6-tetramethylpiperidine-1-oxyl, 6-aza-7,7-dimethyl-spiro(4,5)decane-6-oxyl, 2,2,6,6-tetramethyl-4-acetoxypiperidine-1-oxyl, 2,2,6,6-tetramethyl-4-benzoyloxypiperidine-1-oxyl, and 4,4',4"-tris-(2,2,6,6-tetramethylpiperidine-1-oxyl) phosphite. These polymerization inhibitors may be used either alone respectively or in combinations with each other.

The amount of the above polymerization inhibitor as added is favorably in the range of 0.0001 to 1 weight %, more favorably 0.001 to 0.5 weight %, relative to the amount of the entire raw (meth)acrylic acid to be supplied.

In the present invention production process, the temperature of the reaction between the (meth)acrylic acid and the alkylene oxide is usually set in the range of favorably 40 to 120° C., more favorably 50 to 120° C., still more favorably 50 to 110° C., particularly favorably 50 to 100° C. In the case where the above reaction temperature is lower than 40° C., the reaction rate is too slow, and the gas concentration of the unreacted alkylene oxide in a gas phase is therefore so high that there is a danger of explosion. Therefore, for ensuring the safety, it is necessary to dilute the gas phase portion with an inert gas to thereby lower the gas concentration of the alkylene oxide in the gas phase, so the procedure is complicated. In this case, there may also be economical disadvantages in that it is necessary to raise the designed pressure of the reactor. In addition, there is also a method that involves decelerating the addition rate of the alkylene oxide to thereby lower the concentration of the unreacted alkylene oxide, but this method has a possibility of prolonging the reaction time and thus resulting in low productivity. In addition, in the case where the above reaction temperature is higher than 120° C., there is a possibility that it may be difficult to suppress the side production of the dialkylene glycol mono(meth)acrylate which is the alkylene oxide's diaddition product.

In the present invention production process, the reaction can be carried out at a higher temperature than conventional, and it is therefore possible to shorten the reaction time and to enhance the productivity. In the case of carrying out the reaction at a high temperature, the reaction temperature is favorably higher than the above-mentioned upper limit of the favorable reaction temperature by not less than 3° C., more favorably by 3 to 50° C., still more favorably by 10 to 40° C. In the case where the reaction temperature is higher than the above-mentioned upper limit of the favorable reaction temperature by less than 3° C., there is a case where the effects of shortening the reaction time and enhancing the productivity are not obtained so much. In addition, in the case where the reaction temperature is higher than the above-mentioned upper limit of the favorable reaction temperature by more than 50° C., there is a possibility that: even if the shortening of the reaction time and the enhancement of the productivity can be achieved, the reaction liquid may polymerize to cause clogging of the piping, therefore resulting in low productivity.

In addition, in the case of carrying out the reaction at a high temperature as mentioned above, the same results can be obtained even if the amount of the catalyst as used is reduced to smaller than conventional, and further the side production of impurities derived from the catalyst can also be reduced, therefore it is possible to save the cost and to have consideration for environmental aspects. Incidentally, there is no especial limitation on the above impurities derived from the catalyst. However, specific examples thereof include hydroxyalkyl acetates (e.g. hydroxyethyl acetate and hydroxypropyl acetate) in the case of using the chromium acetate as the catalyst.

In the production steps including a reaction step and a distillation step or including a reaction step, an aging step, and a distillation step in the present invention production process, a diester-formation inhibitor may be added in order to inhibit the side production of the diester (specifically, alkylene glycol di(meth)acrylate) that can be an impurity other than the above alkylene oxide's diaddition product. The above diester-formation inhibitor may be added appropriately in lots if necessary. Favorable examples of the diester-formation inhibitor include at least one compound selected from the group consisting of: carboxylic acids and carboxylic anhydrides, such as oxalic acid, oxalic anhydride, malonic acid, succinic acid, succinic anhydride, fumaric acid, maleic acid, maleic anhydride, salicylic acid, octanoic acid, adipic acid, sebacic acid, tetradecanedicarboxylic acid, 1,2,4-butanetricarboxylic acid, 1,3,6-hexanetricarboxylic acid, 1,2,3,4-butanetetracarboxylic acid, 1,2,3,4-pentanetetracarboxylic acid, 1,6,7,12-dodecanetetracarboxylic acid, benzoic acid, o-toluic acid, m-toluic acid, p-toluic acid, phthalic acid, phthalic anhydride, isophthalic acid, terephthalic acid, 2,6-naphthalenedicarboxylic acid, pyromellitic acid, pyromellitic anhydride, trimellitic acid, trimellitic anhydride, 1,2,4-benzenetricarboxylic acid, 1,4,5,8-naphthalenetetracarboxylic acid, 1,3,5,7-naphthalenetetracarboxylic acid, and poly(acrylic acid); polyhydric alcohols, such as glycerol, diethylene glycol, trimethylolpropane, cresol, 1,2,6-hexanetriol, pentaerythritol, dipentaerythritol, 2,3,4,5-tetrahydroxyhexane, xylitol, mannitol, catechol, resorcin, 2,6-dihydroxytoluene, tert-butylcatechol, pyrogallol, 2,4-bis(hydroxymethyl)phenol, 1,2,4-trihydroxybenzene, 1,3,5-trihydroxybenzene, 2,4,6-tris(hydroxymethyl)phenol, and 1,2,4,5-tetrahydroxybenzene; and metal-chelating agents, such as ethylenediaminetetraacetic acid, ethylenediaminetetrapropionic acid, nitrilotriacetic acid, iminodiacetic acid, 1,2-diaminocyclohexanetetraacetic acid, acetylacetone, cupferron, oxine, benzidine, and diethyldithiocarbamic acid.

In the present invention production process, the reaction may be carried out in a solvent for the purpose of such as mildly running the reaction. Usable as the solvent are, for example, conventional solvents such as toluene, xylene, heptane, and octane.

In the present invention production process, the pressure inside the system during the reaction may be set appropriately for kinds and mixing ratios of raw materials used, but usually a pressurized state is favorable.

In the case where metallic compounds, such as metal salts (e.g. chromium compounds) and metallic complexes, are used as the catalyst in the present invention production process, it is also possible to recover and then recycle the used catalyst.

Specifically, for example, in the case where the reaction is carried out in the coexistence of a metal-ion-containing homogeneous metal catalyst (e.g. a metal salt and a metallic complex) and an anion-exchange resin (basic anion-exchange resin containing at least one kind of basic functional group (e.g. a quaternary phosphonium salt, a tertiary amino group, a quaternary ammonium group, and a pyridinium group)), the homogeneous metal catalyst can be recovered by causing the anion-exchange resin to adsorb the homogeneous metal catalyst with the progress of the reaction (in detail, the homogeneous metal catalyst can be adsorbed when the concentration of the (meth)acrylic acid has decreased to 0.10% near the end of the aging reaction). Then, the adsorbed homogeneous metal catalyst can be freed by bringing the raw (meth)acrylic acid into contact with the anion-exchange resin (having adsorbed the homogeneous metal catalyst) before the next reaction, so that the homogeneous metal catalyst can be recycled.

In the case where the recovery and recycling of the catalyst is carried out by utilizing the resin in the above way, the reaction system temperature has hitherto been further raised (e.g. in the aging step) after the end of the supply of the raw (meth)acrylic acid and the raw alkylene oxide. However, for making it easy to find out the end point of the reaction, it is favorable to drop the above reaction system temperature, because, if it is impossible to find out the end point of the reaction, resulting in too much progress of the reaction, then there is a possibility that the amount of the forming diester (which is a by-product) may increase to deactivate the catalyst.

(Effects and Advantages of the Invention)

The present invention production process can provide a novel production process for a hydroxyalkyl (meth)acrylate, in which it is possible that: in a batch reaction system, the amount of the hydroxyalkyl (meth)acrylate (which is the objective product) as produced is kept nearly on the same level as conventional and further, at the same time, there is suppressed the side production of the alkylene oxide's diaddition product (dialkylene glycol mono(meth)acrylate) that lowers the purity of the product to thus give a bad influence upon its quality.

DETAILED DESCRIPTION OF THE PREFERRED EMBODIMENTS

Hereinafter, the present invention is more specifically illustrated by the following examples of some preferred embodiments in comparison with comparative examples not according to the invention. However, the present invention is not limited to them in any way. Incidentally, hereinafter, for convenience, the units "weight part(s)" and "liter(s)" may be referred to simply as "part(s)" and "L" respectively.

EXAMPLE 1

An SUS-316-made autoclave of 1 L in capacity with a stirrer was charged with 105 g of acrylic acid (as a portion of 420 g in terms of amount of entire acrylic acid to be supplied), 2.10 g of chromium acetate (as a catalyst), and 0.42 g of phenothiazine (as a polymerization inhibitor) ("chromium acetate concentration (2.0 weight %) relative to amount of acrylic acid as charged"/"chromium acetate concentration (0.5 weight %) relative to amount of entire acrylic acid to be supplied"=4.0 (times)), and then internal air of the autoclave was replaced with nitrogen gas, and then the temperature was raised to 80° C. and the internal pressure was adjusted to 0.1 MPa. Ethylene oxide was supplied at 90 g/h for 0.75 hour (67.5 g), and then acrylic acid and ethylene oxide were supplied at 140 g/h and 90 g/h, respectively, both for 2.25 hours (acrylic acid 315 g, ethylene oxide 202.5 g), while 80° C. was kept to carry out a reaction. After the supply of the acrylic acid and the ethylene oxide had been completed, the reaction temperature was kept constant at 80° C. to continue the reaction till the unreacted acrylic acid decreased to 0.10 weight %. As a result of the continuation of the reaction for 1.0 hour, the unreacted acrylic acid decreased to 0.10 weight %, so the reaction liquid was cooled. A gas-chromatographic analysis of the resultant reaction liquid showed a hydroxyethyl acrylate concentration of 93 weight %, a diethylene glycol monoacrylate concentration of 6.3 weight %, an ethylene glycol diacrylate concentration of 0.3 weight %, and a hydroxyethyl acetate concentration of 0.5 weight %. These results are shown in Table 1.

Next, the resultant reaction liquid was transferred into a glass round-bottom flask of 1 L in capacity, and then this flask was set to a vacuum distillation apparatus to carry out purification under a vacuum of 2 to 10 hPa while the reaction liquid was caused to bubble with air at 10 mL/min and heated in the internal temperature range of 60 to 100° C., thus obtaining hydroxyethyl acrylate from the reaction liquid in a distillate yield of 88 weight %.

A gas-chromatographic analysis of the resultant hydroxyethyl acrylate showed its purity of 97.5 weight % and a diethylene glycol monoacrylate (impurity) content of 2.0 weight %.

EXAMPLE 2

An SUS-316-made autoclave of 1 L in capacity with a stirrer was charged with 210 g of acrylic acid (as a portion of 420 g in terms of amount of entire acrylic acid to be supplied), 2.10 g of chromium acetate (as a catalyst), and 0.42 g of phenothiazine (as a polymerization inhibitor) ("chromium acetate concentration (1.0 weight %) relative to amount of acrylic acid as charged"/"chromium acetate concentration (0.5 weight %) relative to amount of entire acrylic acid to be supplied"=2.0 (times)), and then internal air of the autoclave was replaced with nitrogen gas, and then the temperature was raised to 80° C. and the internal pressure was adjusted to 0.1 MPa. Ethylene oxide was supplied at 90 g/h for 1.5 hours (135 g), and then acrylic acid and ethylene oxide were supplied at 140 g/h and 90 g/h, respectively, both for 1.5 hours (acrylic acid 210 g, ethylene oxide 135 g), while 80° C. was kept to carry out a reaction. After the supply of the acrylic acid and the ethylene oxide had been completed, the reaction temperature was kept constant at 80° C. to continue the reaction till the unreacted acrylic acid decreased to 0.10 weight %. As a result of the continuation of the reaction for 1.2 hours, the unreacted acrylic acid decreased to 0.10 weight %, so the reaction liquid was cooled. A gas-chromatographic analysis of the resultant reaction liquid showed a hydroxyethyl acrylate concentration of 92 weight %, a diethylene glycol monoacrylate concentration of 6.6 weight %, an ethylene glycol diacrylate concentration of 0.3 weight %, and a hydroxyethyl acetate concentration of 0.5 weight %. These results are shown in Table 1.

Next, the resultant reaction liquid was transferred into a glass round-bottom flask of 1 L in capacity, and then this flask was set to a vacuum distillation apparatus to carry out purification under a vacuum of 2 to 10 hPa while the reaction liquid was caused to bubble with air at 10 mL/min and heated in the internal temperature range of 60 to 100° C., thus obtaining hydroxyethyl acrylate from the reaction liquid in a distillate yield of 86 weight %.

A gas-chromatographic analysis of the resultant hydroxyethyl acrylate showed its purity of 97.5 weight % and a diethylene glycol monoacrylate (impurity) content of 2.0 weight %.

EXAMPLE 3

An SUS-316-made autoclave of 1 L in capacity with a stirrer was charged with 315 g of acrylic acid (as a portion of 420 g in terms of amount of entire acrylic acid to be supplied), 2.10 g of chromium acetate (as a catalyst), and 0.42 g of phenothiazine (as a polymerization inhibitor) ("chromium acetate concentration (0.67 weight %) relative to amount of acrylic acid as charged"/"chromium acetate concentration (0.5 weight %) relative to amount of entire acrylic acid to be supplied"=1.3 (times)), and then internal air of the autoclave was replaced with nitrogen gas, and then the temperature was raised to 80° C. and the internal pressure was adjusted to 0.1 MPa. Ethylene oxide was supplied at 90 g/h for 2.25 hours (202.5 g), and then acrylic acid and ethylene oxide were supplied at 140 g/h and 90 g/h, respectively, both for 0.75 hour (acrylic acid 105 g, ethylene oxide 67.5 g), while 80° C. was kept to carry out a reaction. After the supply of the acrylic acid and the ethylene oxide had been completed, the reaction temperature was kept constant at 80° C. to continue the reaction till the unreacted acrylic acid decreased to 0.10 weight %. As a result of the continuation of the reaction for 1.5 hours, the unreacted acrylic acid decreased to 0.10 weight %, so the reaction liquid was cooled. A gas-chromatographic analysis of the resultant reaction liquid showed a hydroxyethyl acrylate concentration of 92 weight %, a diethylene glycol monoacrylate concentration of 7.1 weight %, an ethylene glycol diacrylate concentration of 0.3 weight %, and a hydroxyethyl acetate concentration of 0.5 weight %. These results are shown in Table 1.

Next, the resultant reaction liquid was transferred into a glass round-bottom flask of 1 L in capacity, and then this flask was set to a vacuum distillation apparatus to carry out purification under a vacuum of 2 to 10 hPa while the reaction liquid was caused to bubble with air at 10 mL/min and heated in the internal temperature range of 60 to 100° C., thus obtaining hydroxyethyl acrylate from the reaction liquid in a distillate yield of 83 weight %.

A gas-chromatographic analysis of the resultant hydroxyethyl acrylate showed its purity of 97.5 weight % and a diethylene glycol monoacrylate (impurity) content of 2.0 weight %.

EXAMPLE 4

An SUS-316-made autoclave of 1 L in capacity with a stirrer was charged with 105 g of acrylic acid (as a portion of 420 g in terms of amount of entire acrylic acid to be supplied), 2.10 g of chromium acetate (as a catalyst), and 0.42 g of phenothiazine (as a polymerization inhibitor) ("chromium acetate concentration (2.0 weight %) relative to amount of acrylic acid as charged"/"chromium acetate concentration (0.5 weight %) relative to amount of entire acrylic acid to be supplied"=4.0 (times)), and then internal air of the autoclave was replaced with nitrogen gas, and then the temperature was raised to 90° C. and the internal pressure was adjusted to 0.1 MPa. Ethylene oxide was supplied at 90 g/h for 0.75 hour (67.5 g), and then acrylic acid and ethylene oxide were supplied at 140 g/h and 90 g/h, respectively, both for 2.25 hours (acrylic acid 315 g, ethylene oxide 202.5 g), while 90° C. was kept to carry out a reaction. After the supply of the acrylic acid and the ethylene oxide had been completed, the reaction temperature was kept constant at 90° C. to continue the reaction till the unreacted acrylic acid decreased to 0.10 weight %. As a result of the continuation of the reaction for 0.7 hour, the unreacted acrylic acid decreased to 0.10 weight %, so the reaction liquid was cooled. A gas-chromatographic analysis of the resultant reaction liquid showed a hydroxyethyl acrylate concentration of 93 weight %, a diethylene glycol monoacrylate concentration of 5.9 weight %, an ethylene glycol diacrylate concentration of 0.4 weight %, and a hydroxyethyl acetate concentration of 0.5 weight %. These results are shown in Table 1.

Next, the resultant reaction liquid was transferred into a glass round-bottom flask of 1 L in capacity, and then this flask was set to a vacuum distillation apparatus to carry out purification under a vacuum of 2 to 10 hPa while the reaction liquid was caused to bubble with air at 10 mL/min and heated in the internal temperature range of 60 to 100° C., thus obtaining hydroxyethyl acrylate from the reaction liquid in a distillate yield of 91 weight %.

of the reaction for 2.2 hours, the unreacted acrylic acid decreased to 0.10 weight %, so the reaction liquid was cooled. A gas-chromatographic analysis of the resultant reaction liquid showed a hydroxyethyl acrylate concentration of 91 weight %, a diethylene glycol monoacrylate concentration of 7.3 weight %, an ethylene glycol diacrylate concentration of 0.4 weight %, and a hydroxyethyl acetate concentration of 0.5 weight %. These results are shown in Table 1.

Next, the resultant reaction liquid was transferred into a glass round-bottom flask of 1 L in capacity, and then this flask was set to a vacuum distillation apparatus to carry out purification under a vacuum of 2 to 10 hPa while the reaction liquid was caused to bubble with air at 10 mL/min and heated in the internal temperature range of 60 to 100° C., thus obtaining hydroxyethyl acrylate from the reaction liquid in a distillate yield of 81 weight %.

A gas-chromatographic analysis of the resultant hydroxyethyl acrylate showed its purity of 97.5 weight % and a diethylene glycol monoacrylate (impurity) content of 2.0 weight %.

TABLE 1

| | Chromium acetate concentration relative to acrylic acid | | | Reaction temperature (° C.) | Reaction time (h) | Composition of reaction liquid | | | | Distillate yield (%) |
| --- | --- | --- | --- | --- | --- | --- | --- | --- | --- | --- |
| | ① Amount as charged (wt %) | ② Entire amount to be supplied (wt %) | ①/② | | | HEA (wt %) | DEGMA (wt %) | EGDA (wt %) | EGAc (wt %) | |
| Example 1 | 2.0 | 0.5 | 4.0 | 80 | 4.0 | 93 | 6.3 | 0.3 | 0.5 | 88 |
| Example 2 | 1.0 | 0.5 | 2.0 | 80 | 4.2 | 92 | 6.6 | 0.3 | 0.5 | 86 |
| Example 3 | 0.7 | 0.5 | 1.3 | 80 | 4.5 | 92 | 7.1 | 0.3 | 0.5 | 83 |
| Example 4 | 2.0 | 0.5 | 4.0 | 90 | 3.7 | 93 | 5.9 | 0.4 | 0.5 | 91 |
| Comparative Example 1 | 0.5 | 0.5 | 1.0 | 80 | 5.2 | 91 | 7.3 | 0.4 | 0.5 | 81 |

(Notes)
HEA: Hydroxyethyl acrylate
DEGMA: Diethylene glycol monoacrylate
EGDA: Ethylene glycol diacrylate
EGAc: Hydroxyethyl acetate A gas-chromatographic analysis of the resultant hydroxyethyl acrylate showed its purity of 97.5 weight % and a diethylene glycol monoacrylate (impurity) content of 2.0 weight %.

COMPARATIVE EXAMPLE 1

An SUS-316-made autoclave of 1 L in capacity with a stirrer was charged with 420 g of acrylic acid, 2.10 g of chromium acetate (as a catalyst), and 0.42 g of phenothiazine (as a polymerization inhibitor), and then internal air of the autoclave was replaced with nitrogen gas, and then the temperature was raised to 80° C. and the internal pressure was adjusted to 0.1 MPa. Ethylene oxide was supplied at 90 g/h for 3 hours (270 g), while 80° C. was kept to carry out a reaction. After the supply of the ethylene oxide had been completed, the reaction temperature was kept constant at 80° C. to continue the reaction till the unreacted acrylic acid decreased to 0.10 weight %. As a result of the continuation

EXAMPLE 5

An SUS-316-made autoclave of 1 L in capacity with a stirrer was charged with 112 g of methacrylic acid (as a portion of 448 g in terms of amount of entire methacrylic acid to be supplied), 0.45 g of chromium acetate (as a catalyst), and 0.45 g of phenothiazine (as a polymerization inhibitor) ("chromium acetate concentration (0.4 weight %) relative to amount of methacrylic acid as charged"/"chromium acetate concentration (0.1 weight %) relative to amount of entire methacrylic acid to be supplied"=4.0 (times)), and then internal air of the autoclave was replaced with nitrogen gas, and then the temperature was raised to 90° C. and the internal pressure was adjusted to 0.1 MPa. Ethylene oxide was supplied at 80 g/h for 0.75 hour (60.2 g), and then methacrylic acid and ethylene oxide were supplied at 149 g/h and 80 g/h, respectively, both for 2.25 hours (methacrylic acid 336 g, ethylene oxide 180.5 g), while 90° C. was kept to carry out a reaction. After the supply of the methacrylic acid and the ethylene oxide had been completed, the reaction temperature was kept constant at 90° C. to continue the reaction till the unreacted methacrylic acid decreased to 0.10 weight %. As a result of the continuation of the reaction for 1.5 hours, the unreacted methacrylic acid decreased to 0.10 weight %, so the reaction liquid was cooled. A gas-chromatographic analysis of the resultant reaction liquid showed a hydroxyethyl methacrylate concentration of 95 weight %, a diethylene glycol monomethacrylate concentration of 3.5 weight %, an ethylene glycol dimethacrylate concentration of 0.1 weight %, and a hydroxyethyl acetate concentration of 0.12 weight %. These results are shown in Table 2.

EXAMPLE 6

An SUS-316-made autoclave of 1 L in capacity with a stirrer was charged with 224 g of methacrylic acid (as a portion of 448 g in terms of amount of entire methacrylic acid to be supplied), 0.68 g of chromium acetate (as a catalyst), and 0.45 g of phenothiazine (as a polymerization inhibitor) ("chromium acetate concentration (0.30 weight %) relative to amount of methacrylic acid as charged"/ "chromium acetate concentration (0.15 weight %) relative to amount of entire methacrylic acid to be supplied"=2.0 (times)), and then internal air of the autoclave was replaced with nitrogen gas, and then the temperature was raised to 90° C. and the internal pressure was adjusted to 0.1 MPa. Ethylene oxide was supplied at 80 g/h for 1.5 hours (120 g), and then methacrylic acid and ethylene oxide were supplied at 149 g/h and 80 g/h, respectively, both for 1.5 hours (methacrylic acid 224 g, ethylene oxide 120 g), while 90° C. was kept to carry out a reaction. After the supply of the methacrylic acid and the ethylene oxide had been completed, the reaction temperature was kept constant at 90° C. to continue the reaction till the unreacted methacrylic acid decreased to 0.10 weight %. As a result of the continuation of the reaction for 1.5 hours, the unreacted methacrylic acid decreased to 0.10 weight %, so the reaction liquid was cooled. A gas-chromatographic analysis of the resultant reaction liquid showed a hydroxyethyl methacrylate concentration of 95 weight %, a diethylene glycol monomethacrylate concentration of 3.5 weight %, an ethylene glycol dimethacrylate concentration of 0.1 weight %, and a hydroxyethyl acetate concentration of 0.16 weight %. These results are shown in Table 2.

COMPARATIVE EXAMPLE 2

An SUS-316-made autoclave of 1 L in capacity with a stirrer was charged with 448 g (=amount of entire methacrylic acid to be supplied) of methacrylic acid, 0.90 g of chromium acetate (as a catalyst), and 0.45 g of phenothiazine (as a polymerization inhibitor), and then internal air of the autoclave was replaced with nitrogen gas, and then the temperature was raised to 90° C. and the internal pressure was adjusted to 0.1 MPa. Ethylene oxide was supplied at 80 g/h for 3.0 hours (240 g), while 90° C. was kept to carry out a reaction. After the supply of the ethylene oxide had been completed, the reaction temperature was kept constant at 90° C. to continue the reaction till the unreacted methacrylic acid decreased to 0.10 weight %. As a result of the continuation of the reaction for 1.6 hours, the unreacted methacrylic acid decreased to 0.10 weight %, so the reaction liquid was cooled. A gas-chromatographic analysis of the resultant reaction liquid showed a hydroxyethyl methacrylate concentration of 95 weight %, a diethylene glycol monomethacrylate concentration of 3.6 weight %, an ethylene glycol dimethacrylate concentration of 0.1 weight %, and a hydroxyethyl acetate concentration of 0.21 weight %. These results are shown in Table 2.

COMPARATIVE EXAMPLE 3

An SUS-316-made autoclave of 1 L in capacity with a stirrer was charged with 448 g (=amount of entire methacrylic acid to be supplied) of methacrylic acid, 0.45 g of chromium acetate (as a catalyst), and 0.45 g of phenothiazine (as a polymerization inhibitor), and then internal air of the autoclave was replaced with nitrogen gas, and then the temperature was raised to 90° C. and the internal pressure was adjusted to 0.1 MPa. Ethylene oxide was supplied at 80 g/h for 3.0 hours (240 g), while 90° C. was kept to carry out a reaction. After the supply of the ethylene oxide had been completed, the reaction temperature was kept constant at 90° C. to continue the reaction till the unreacted methacrylic acid decreased to 0.10 weight %. As a result of the continuation of the reaction for 2.8 hours, the unreacted methacrylic acid decreased to 0.10 weight %, so the reaction liquid was cooled. A gas-chromatographic analysis of the resultant reaction liquid showed a hydroxyethyl methacrylate concentration of 93 weight %, a diethylene glycol monomethacrylate concentration of 5.8 weight %, an ethylene glycol dimethacrylate concentration of 0.2 weight %, and a hydroxyethyl acetate concentration of 0.12 weight %. These results are shown in Table 2.

TABLE 2

|  | Chromium acetate concentration relative to methacrylic acid | | | | Composition of reaction liquid | | | |
| --- | --- | --- | --- | --- | --- | --- | --- | --- |
|  | ① Amount as charged (wt %) | ② Entire amount to be supplied (wt %) | ①/② | Reaction time (h) | HEMA (wt %) | DEGMMA (wt %) | EGDMA (wt %) | EGAc (wt %) |
| Example 5 | 0.40 | 0.10 | 4.0 | 4.5 | 95 | 3.5 | 0.1 | 0.12 |
| Example 6 | 0.30 | 0.15 | 2.0 | 4.5 | 95 | 3.5 | 0.1 | 0.16 |
| Comparative Example 2 | 0.20 | 0.20 | 1.0 | 4.6 | 95 | 3.6 | 0.1 | 0.21 |
| Comparative Example 3 | 0.10 | 0.10 | 1.0 | 5.8 | 93 | 5.8 | 0.2 | 0.12 |

(Notes)
HEMA: Hydroxyethyl methacrylate
DEGMMA: Diethylene glycol monomethacrylate
EGDMA: Ethylene glycol dimethacrylate
EGAc: Hydroxyethyl acetate Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A production process for a hydroxyalkyl (meth)acrylate, which comprises the step of carrying out a batch reaction between (meth)acrylic acid and an alkylene oxide in the presence of a catalyst in order to produce the hydroxyalkyl (meth)acrylate, wherein the batch reaction includes the steps of:
    a) initiating the batch reaction in a state of a catalyst concentration of more than 1, wherein the catalyst concentration is defined as the amount of the catalyst as used relative to the integrated amount of the (meth)acrylic acid as supplied and is assumed to be 1 in terms of the amount of the entire catalyst to be used relative to the amount of the entire (meth)acrylic acid to be supplied;
    b) providing the catalyst to include at least one member selected from the group consisting of chromium (Cr) compounds, iron (Fe) compounds, yttrium (Y) compounds, lanthanum (La) compounds, cerium (Ce) compounds, tungsten (W) compounds, zirconium (Zr) compounds, titanium (Ti) compounds, vanadium (V) compounds, phosphorous (P) compounds, aluminum (Al) compounds, molybdenum (Mo) compounds and amine compounds;
    c) providing the alkylene oxide to have 2 to 6 carbon atoms;
    d) charging an initial charge amount of said (meth)acrylic acid to a vessel, with said initial charge amount being a portion of an entire amount of raw (meth)acrylic acid to be supplied to said batch reaction, with said portion of raw (meth)acrylic acid and a residual amount of raw (meth)acryiic acid being equal to said entire amount of raw (meth)acrylic acid to be supplied to the batch reaction; then
    e) gradually adding a portion of an entire amount of alkylene oxide to said initial charge amount of said (meth)acrylic acid in said vessel until an amount of alkylene oxide is in a range of 0.8 to 2.0 in terms of molar ratio to said initial charge amount of said (meth)acrylic acid, with said portion of alkylene oxide and a residual amount of alkylene oxide being equal to said entire amount of alkylene oxide to be supplied to the batch reaction, with (meth)acrylic acid not being added in this step "e"; and then
    f) adding, after said amount of alkylene oxide is in said range, said residual amounts of said (meth)acrylic acid and alkylene oxide to said vessel such that said entire amounts of raw (meth)acrylic acid and alkylene oxide have been supplied to the batch reaction.

2. A production process for a hydroxyalkyl (meth)acrylate, which comprises the step of carrying out a batch reaction between (meth)acrylic acid and an alkylene oxide in order to produce the hydroxyalkyl (meth)acrylate, wherein the batch reaction includes the steps of:
    a) providing the alkylene oxide to have 2 to 6 carbon atoms;
    b) charging an initial charge amount of said (meth)acrylic acid to a vessel, with said initial charge amount being a portion of an entire amount of raw (meth)acrylic acid to be supplied to said batch reaction, with said portion of raw (meth)acrylic acid and a residual amount of raw (meth)acrylic acid being equal to said entire amount of raw (meth)acrylic acid to be supplied to the batch reaction; then
    c) gradually adding a portion of an entire amount of alkylene oxide to said initial charge amount of said (meth)acrylic acid in said vessel until an amount of alkylene oxide is in a range of 0.8 to 2.0 in terms of molar ratio to said initial charge amount of said (meth)acrylic acid, with said portion of alkylene oxide and a residual amount of alkylene oxide being equal to said entire amount of alkylene oxide to be supplied to the batch reaction, with (meth)acrylic acid not being added in this step "c"; and then
    d) adding, after said amount of alkylene oxide is in said range, said residual amounts of said (meth)acryiic acid and alkylene oxide to said vessel such that said entire amounts of raw (meth)acrylic acid and alkylene oxide have beensupplied to the batch reaction.

3. A production process according to claim 2, with said residual amounts being added together to the batch reaction by a lump-sum addition.

4. A production process according to claim 2, with said residual amounts being added together to the batch reaction by a gradual addition.

5. A production process according to claim 2, with said residual amounts being added together to the batch reaction between 0.1 hours and 5 hours beyond commencement of said initial stage to minimize production of a diaddition by-product of said alkylene oxide.

6. A production process according to claim 2, with said residual amount of alkylene oxide being in a range of 0.8 to 2.0 in terms of molar ratio to said residual amount of (meth)acrylic acid.

7. A production process according to claim 2, wherein said initial charge amount of (meth)acrylic acid is in a range of 5 to 90 weight % of an entire amount of (meth)acrylic acid.

* * * * *